United States Patent [19]

Bundgaard, deceased et al.

[11] Patent Number: 5,306,841

[45] Date of Patent: Apr. 26, 1994

[54] DERIVATIVES OF INOSITOL, PREPARATIONS CONTAINING THEM AND THEIR USE

[76] Inventors: Hans Bundgaard, deceased, late of Horsholm, Denmark; by Charlotte Bundgaard, legal representative, Tjorneveg 36, Horsholm, Denmark, DK-2970

[21] Appl. No.: 955,708

[22] PCT Filed: Jun. 30, 1992

[86] PCT No.: PCT/SE92/00489

§ 371 Date: Jul. 2, 1993

§ 102(e) Date: Jul. 2, 1993

[87] PCT Pub. No.: WO93/01197

PCT Pub. Date: Jan. 21, 1993

[30] Foreign Application Priority Data

Jul. 3, 1991 [SE] Sweden .................. 91 02068

[51] Int. Cl.$^5$ .................. C07F 9/117; C07F 9/144; C07F 9/40; A61K 31/66

[52] U.S. Cl. .................. 558/160; 558/155; 558/156; 558/179; 558/180; 558/194; 558/208; 558/214

[58] Field of Search .......... 558/160, 180, 155, 156, 558/179, 194, 208, 214

[56] References Cited

U.S. PATENT DOCUMENTS

| | | | |
|---|---|---|---|
| 4,515,722 | 5/1985 | Yang et al. | 260/403 |
| 4,585,762 | 4/1986 | Teraji et al. | 514/129 |
| 4,797,390 | 1/1989 | Siren | 514/103 |
| 5,157,140 | 10/1992 | Siren | 558/155 |

FOREIGN PATENT DOCUMENTS 0269105 11/1987 European Pat. Off. ..... C07F 9/117

OTHER PUBLICATIONS

*Biochem. Biophys. Res. Commun.*, vol. 120; 2, pp. 481–485 (1984); Suematsu et al.

*Primary Examiner*—Marianne M. Cintins
*Assistant Examiner*—Michael B. Hydorn
*Attorney, Agent, or Firm*—Scully, Scott, Murphy & Presser

[57] ABSTRACT

A compound having the formula

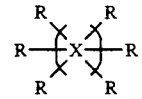

where X is a radical of myo-inositol or a radical of a configuration isomer thereof where at least one R is

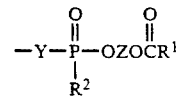

where Y is (1) oxygen, (2) a straight or branched alkyl with 1–10 carbon atoms, where Z is (1)

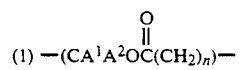

where $A^1$ and $A^2$ are the same or different and are hydrogen or methyl and n is 3–10, or (2)

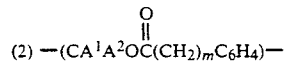

where $A^1$ and $A^2$ are hydrogen or methyl and where m is 1–5, where $R^1$ is hydrogen, straight or branched alkyl, aryl or alkaryl, alkoxy or aryloxy, where $R^2$ is
(1) $R^1$,
(2) hydroxyl, or
(3) OZOCOR$^1$,
and where the remaining R is/are hydroxyl.

4 Claims, No Drawings

DERIVATIVES OF INOSITOL, PREPARATIONS CONTAINING THEM AND THEIR USE

FIELD OF INVENTION

The present invention relates to novel derivatives of different phosphorus-containing isomers of inositol and compositions containing the same.

BACKGROUND OF THE INVENTION

The family of hexahydroxy derivatives of cyclohexane is known as inositols. There exist nine different isomers and one of these, myo-inositol, is of biological importance. Chiro-inositols and scyllo-inositols are also naturally occurring but very little is known about their biological role.

Myo-inositol is an essential nutrient for microorganisms and under special dietary conditions for different animals.

There are some known derivatives of myo-inositol such as phosphates and phospholipids.

Myo-inositol is found in plants primarily as its hexaphosphate ester, i.e. phytic acid.

Different specific isomers of myo-inositol phosphates such as D-myo-inositol1,4,5-trisphosphate has been reported in Biochem. Biophys. Res. Commun. 120.2 (1984) p. 481. This compound is known as an intracelluar calcium mobilizer in mammalian cells. Other specific isomers of myo-inositol trisphosphate have been disclosed in the U.S. Pat. No. 4,797,390. Compounds described in the above mentioned patent are used for example in pharmaceutical preparation.

Despite the ionic structure of the compounds the pharmacological effect of these compounds is very significant also after oral administration. However, in order to improve the penetration through biological membranes different lipophilic derivatives of inositol phosphates have been disclosed in the European Patent Application No. 269105. Examples of these are acyloxyalkylesters of inositol phosphates where the phosphate substituents are further esterified with acyloxyalkyl moities.

In certain biological systems it is desirable that the substituents on the inositol phosphate compounds are removed after the penetration of cellular membranes. For example after oral administration of an inositol phosphate derivative it is in many cases important to design the derivative in such a way that the original compound is formed in the blood stream. After the penetration of cell membranes for example esterified inositol phosphates are degraded enzymatically by different forms of esterases. However, in many cases the degradation process is quite slow and thus the formation of the requested compound is retarded.

SUMMARY OF THE INVENTION

According to the present invention it has quite unexpectedly been possible to produce novel derivatives of inositol in pure form.

A compound having the formula

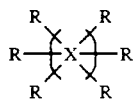

(I)

has been produced with high purity wherein X is a radical of myo-inositol or a radical of a configuration isomer thereof
wherein at least one of R is

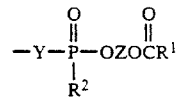

wherein Y is
(1) oxygen
(2) a straight or branched alkyl
wherein Z is

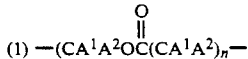

where $A^1$ and $A^2$ are the same or different and are hydrogen, alkyl, aryl, aralkyl, alkenyl, cycloalkyl or cycloalkenyl and n is 3–10

where $A^1$ and $A^2$ are as described above and where m is 1–5

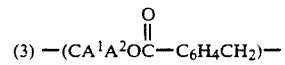

where $A^1$ and $A^2$ are as described above wherein $R^1$ is hydrogen, straight or branched alkyl, alkenyl, aryl, alkaryl, alkoxy or aryloxy, wherein $R^2$ is
(1) $R^1$
(2) hydroxyl
(3) —OZOCOR$^1$
(4) alkoxy or aryloxy
and wherein the remaining R is/are hydroxyl.

In the above definition alkyl means a straight or branched chain preferably containing 1 to 10 carbon atoms such as methyl, ethyl, propyl, isopropyl, butyl, t-butyl, pentyl, hexyl, heptyl or octyl. Alkenyl designates a straight or branched chain preferably containing 2 to 6 carbon atoms such as propenyl, butenyl or pentenyl. Aryl means radicals such as phenyl and naphtyl while cycloalkyl means a structure containing preferably 4 to 7 carbon atoms such as cyclohexyl. Alkoxy means a straight or branched chain containing 1 to 10 carbon atoms such as methoxy, ethoxy, propyloxy, butyloxy and hexyloxy whereas aryloxy contains 6–12 carbon atoms and means phenyloxy or naphtyloxy.

The above mentioned radicals are unsubstituted or substituted with substituents such as alkyl, alkoxy, alkylthio, halogen, amino or hydroxyl.

The described compounds of formula (I) are inositol phosphates and inositol phosphonates substituted with specific forms of acyloxyalkyl moities. After the penetration of cell membranes esterified inositol phosphates and inositol phosphonates are normally degraded to some extent by enzymes such as esterases.

According to this invention the acyloxyalkyl moities are selected in such a way that the distance between the cleavage site for the esterase i.e. the ester group —OCO($R^1$) and the negative charge(s) of the phosphate or phosphonate group is long enough to outbalance the inhibitory effect of the negative charge on the enzymatic activity.

The compounds of formula (I) are thus bioreversibly protected in such a way that the original inositol phosphate or inositol phosphonate is formed in a controlled way in biological systems.

According to the invention X is a radical of myo-inositol or a radical of a configuration isomer thereof. The configuration isomer of myo-inositol is selected from the group of allo-inositol, cis-inositol, chiro-inositol, epi-inositol, muco-inositol, neo-inositol and scyllo-inositol.

The inositol radical can be substituted with one to six substituents containing phosphorus atoms such as inositolmonophosphate, inositolbisphosphate, inositoltrisphosphate, inositoltetraphosphate, inositolpentaphosphate and inositolhexaphosphate.

In one preferred embodiment of the invention X is a radical of myo-inositol.

In another preferred embodiment of the invention Z is $-CH_2OCO(CH_2)_3-$.

One preferred embodiment of this invention is described by the following formula

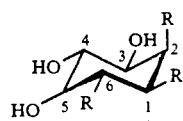   (II)

wherein R is

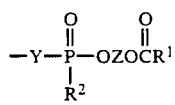

wherein Y, Z, $R^1$ and $R^2$ are as defined previously

In one of the most preferred embodiments of this type of the invention Y is oxygen.

In another preferred embodiment of this type of the invention Y is oxygen and Z is $-CH_2OCO(CH_2)_n-$, n is 3–10, and $R^1$ is $CH_3-$ or $C_6H_5CH_2-$.

Formula II represents derivatives of D-myo-inositol-1,2,6-trisphosphate. Other compounds falling within the scope of the invention are for example acyloxyalkyl esters of D-myo-inositol-1,4,5-trisphosphate and D-myo-inositol-1,3,4,5-tetraphosphate.

The compounds of formula I may be administered orally, topically, parenterally, rectally or by inhalation spray in dosage forms or formulations containing conventional carriers, adjuvants and vehicles.

For oral use, for example, tablets, troches, lozenges, aqueous suspensions, solutions, dispersible powders or granules, capsules and syrups can be utilized.

For topical use creams, ointments, gels and solutions containing the compound can be used.

The described compounds could per se be e.g. pharmaceutically active compounds. The invention also relates to a composition comprising one or more compounds of formula (I) as defined previously. The composition usually contains 10 to 99.5% preferably 20 to 99.5% of these compounds. The inventions relates to the above mentioned compounds as pharameceutically active substances, their use for the manufacture of pharmaceutical preparations and to pharmaceutical preparations containing these compounds.

The following examples illustrate the invention but do not limit the scope of the invention. Those skilled in the art will appreciate that the present invention has a number of potential applications and a variety of possible embodiments.

EXAMPLE 1

A silver salt of D-myo-inositol-1,2,6-trisphosphate was obtained from the corresponding compound in acid form by adding silver nitrate and by raising the pH to 8. 0.8 g of the silver salt was suspended in 30 ml of acetonitrile and 2.5 molar excess of iodomethyl 4-acetoxybutyrate was added. The reaction was continued for 8 hours at 30° C. After filtration the reaction mixture was loaded on a semi-preparative $C_{18}$-column and eluted with acetonitrile/water: 80/20 (by volume). The different collected fractions were investigated by NMR. One fraction with a yield of 53% was identified as D-myo-inositol-1,2,6-tris(4-acetoxybutyryloxymethyl hydrogen) phosphate.

EXAMPLE 2

The compound obtained in example 1 was converted to the sodium salt with a cation exchanger procedure. Tablets of D-myo-inositol-1,2,6-tris(4-acetoxybutyryloxymethyl sodium) phosphate were produced in the following way: 40 g of the sodium salt, 132 g lactose and 6 g acacia were mixed. Purified water was then added to the mixture, whereupon the mixing was continued until a stable consistency was obtained. The mixture was sieved and dried. Then the mixture was blended with 10 g talcum and 2 g magnesium stearate. The mixture was compressed into tablets each weighing 200 mg.

EXAMPLE 3

1.2 g of the silver salt of D-myo-inositol-1,2,6-trisphosphate was stirred in 40 ml acetonitrole and a 1.8 molar excess of iodomethyl-4-valeryloxybutyrate was added. The reaction was continued for 10 hrs at 35° C. After filtration the reaction mixture was loaded on a semi-preparative $C_{18}$-column and was eluted with acetonitrole/water: 80/20. One of the eluted fractions was identified with NMR to be D-myo-inositol-1,2,6-tris(4-valeryloxybutyryloxymethyl hydrogen)phosphate. $^1$HNMR (CDCl$_3$): 5.56, 4.11, 2.44, 1.92, 1.15 and 0.86.

EXAMPLE 4

The sodium salt of the compound manufactured according to example 3 was injected into pigs for evaluation of the hydrolysis in vivo. Three minipigs (weight approx 13 kg) were injected with 150 μmoles of D-myo-inositol-1,2,6-(4-valeryloxybutyryloxy)sodium phosphate each while another group of three animals received an intravenous injection of D-myo-inositoltrisphosphate (IP$_3$). Plasma samples at different time periods were assayed for IP$_3$ and the mean values for the two groups were compared. The relative amount of IP$_3$ formed in the plasma from the animals where the derivative of IP$_3$ was injected compared to the amount of IP$_3$ in the plasma from the animals injected with IP$_3$ during a specific time period demonstrate the conversion in vivo. It was calculated that during the dirst six hours after the injection approximately 10% of D-myo-inositol-1,2,6-tris(4-valeryloxybutyryloxy)sodium phosphate was converted to IP$_3$.

I claim:

1. A compound having the formula

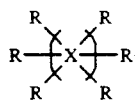

where X is a radical of myo-inositol or a radical of a configuration isomer thereof where at least one R is

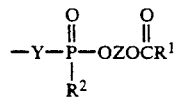

where Y is
(1) oxygen or
(2) a straight or branched alkyl with 1-10 carbon atoms, where Z is

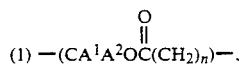

where $A^1$ and $A^2$ are the same or different and are hydrogen or methyl and n is 3-10, or

where $A^1$ and $A^2$ are hydrogen or methyl and where m is 1-5, where $R^1$ is hydrogen, straight or branched alkyl, aryl or alkaryl, alkoxy or aryloxy, where $R^2$ is
(1) $R^1$,
(2) hydroxyl or
(3) $OZOCOR^1$, and where the remaining R is/are hydroxyl.

2. A compound according to claim 1 wherein X is a radical of myo-inositol.

3. A compound according to claim 1 wherein Z is $-CH_2OCO(CH_2)_3-$.

4. A compound according to claim 1 having the formula

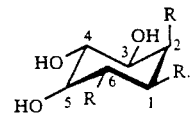

* * * * *